United States Patent [19]

Parab

[11] Patent Number: 5,420,106
[45] Date of Patent: May 30, 1995

[54] METHOD AND COMPOSITION HAVING ENHANCED ALPHA-HYDROXY ACID SKIN PERMEATION AND RETENTION

[75] Inventor: Prakash Parab, Williamsville, N.Y.

[73] Assignee: Bristol-Myers Squibb Company, New York, N.Y.

[21] Appl. No.: 215,984

[22] Filed: Mar. 22, 1994

[51] Int. Cl.⁶ .................... A61K 7/00; A61K 31/40
[52] U.S. Cl. .................... 514/2; 424/401; 424/443; 424/445; 424/447; 514/12; 514/19; 514/844; 514/887; 514/947
[58] Field of Search ............... 424/401, 443, 444, 445, 424/447; 514/887, 844, 947, 2, 12, 19

[56] References Cited

U.S. PATENT DOCUMENTS

| 3,879,537 | 4/1975 | Van Scott et al. | 514/947 |
| 4,105,783 | 8/1978 | Yu et al. | 424/401 |
| 4,363,815 | 12/1982 | Yu et al. | 424/401 |
| 4,732,892 | 3/1988 | Sarpotdar et al. | 514/947 |
| 5,041,437 | 8/1991 | Yoshida et al. | 514/929 |
| 5,059,427 | 10/1991 | Yoshida et al. | 514/906 |
| 5,073,369 | 12/1991 | Frobel et al. | 514/253 |
| 5,087,620 | 2/1992 | Parab | 514/947 |
| 5,091,171 | 2/1992 | Yu et al. | 514/2 |
| 5,254,343 | 10/1993 | Parab et al. | 424/401 |
| 5,306,729 | 4/1994 | Spiegelman et al. | 514/912 |

*Primary Examiner*—Ronald W. Griffin
*Attorney, Agent, or Firm*—Morton S. Simon

[57] ABSTRACT

Methods of enhancing skin permeation and skin retention of α-hydroxy acids for the treatment of dermatological disorders by applying a composition containing an amphoteric salt of an α-hydroxy acid, such as lactic, glycolic, citric, tartaric or malic acid and an amino acid, dipeptide, polypeptide or proteins, in a dermatologically acceptable carrier which contains 0.5 to 8% glycerol monocaprylate, 0 to 80% petrolatum and 0 to 30% isopropyl myristrate, the pH of the composition being from 3 to 9, and compositions for practicing such methods.

9 Claims, 11 Drawing Sheets

METHOD AND COMPOSITION HAVING ENHANCED ALPHA-HYDROXY ACID SKIN PERMEATION AND RETENTION

FIELD OF THE INVENTION

This invention relates to topical administration of therapeutic compositions for the treatment of determatological disorders and to compositions employed for such administration. More particularly, it relates to topical administration of therapeutically effective amounts of amphoteric salts of α-hydroxy acids, such as lactic acid salts of amino acids, in topical compositions that contain selected amounts of glyceryl monocaprylate (GMC) and have a selected pH range. The compositions provide enhanced permeation of the lactic acid into the skin and substantial retention therein.

BRIEF DESCRIPTION OF THE PRIOR ART

The topical use of α-hydroxy acids and α-keto acids for treatment of various skin conditions is well known in the art. It is described, for example, in U.S. Pat. Nos. 3,879,537; 4,105,783 and 4,363,815.

U.S. Pat. No. 5,091,171 describes the employment of various α-hydroxyacids, α-ketoacids and their derivatives, in the form of various salts, particularly amphoteric salts obtained by reaction of the hydroxy acids or ketoacids with amines, especially amphoteric amines such as amino acids, dipeptides, polypeptides and proteins. Typical therapeutically useful salts described in the patent include, for example, lysine lactate, a salt obtained by reaction between lysine and the α-hydroxy acid, lactic acid.

The patent also describes the use of ammonium salts of α-hydroxy acids such as ammonium lactate, stating that the composition, while retaining some of its effects for certain cosmetic conditions, has lost most of its potency for other dermatological disorders. Patentees conclude ammonium lactate exhibits less skin permeation of lactic acid than the other amphoteric salts of lactic acid described in the patent.

Despite this adverse teaching, the art has utilized topical ammonium lactate compositions for various therapeutic purposes. One reason for this acceptance is that, contrary to the teaching of U.S. Pat. No. 5,091,171, ammonium lactate does, in fact, have a high permeation profile for lactic acid. Moreover, it has been surprisingly found that the amphoteric salts of α-hydroxy acid and amino acid, have a poor skin permeation profile for α-hydroxy acid as compared to the corresponding ammonium salts.

A problem associated with the use of ammonium lactate is that it is a skin irritant to a degree which many patients find unacceptable. Amino acids are known to have moisturizing effects on mammalian skin. Amphoteric α-hydroxy acid amino acid salts, therefore, should afford less skin irritation than the corresponding ammonium salts. However, as stated, they exhibit substantially poorer skin permeation of α-hydroxy acid than the corresponding ammonium salts.

There is need for amino acid salts of α-hydroxy acids that have skin permeation of the α-hydroxy acid comparable to that observed with ammonium salts of such acids while having less skin irritation than such ammonium salts. The present invention teaches compositions and methods which enhance skin permeation and skin retention of α-hydroxy acids, particularly lactic acid in the form of amphoteric salts. In essence, the present invention is the discovery that selected amphoteric amino acid salts of α-hydroxy acids, particularly lactic acid, offer equal, or even better, skin permeation than the corresponding ammonium salts when incorporated in the dermatologically acceptable compositions described herein.

SUMMARY OF THE INVENTION

Novel compositions for the treatment of dermatological disorders have now been discovered. They comprise compositions for topical administration to patients in need of such treatment, the compositions containing a dermatologically effective amount of an amphoteric salt of an α-hydroxy acid in a dermatologically acceptable pharmaceutical carrier containing from about 0.5% to 8% of GMC. The compositions are further characterized by a pH range of from about 3 to 9, preferably 3.5 to 6.5 and most preferably 3.8 to 5. Within this pH range, the α-hydroxy acid forms an amphoteric salt with the selected base. The optimum pH for the formation of a specific salt will depend upon the basicity of the selected salt forming reagent, i.e. its pK value. These novel compositions manifest a degree of skin permeation and retention of α-hydroxy acid which is, surprisingly, substantially equivalent to, and in some instances better than, the ammonium salt of such acid.

The skin permeation of α-hydroxy acids, present in the compositions of the invention as the α-hydroxy acid amphoteric salts, is even further improved by addition to such compositions of selected amounts of isopropyl myristrate (IPM) and/or petrolatum (PET).

DETAILED DESCRIPTION OF THE INVENTION

Figure 1:
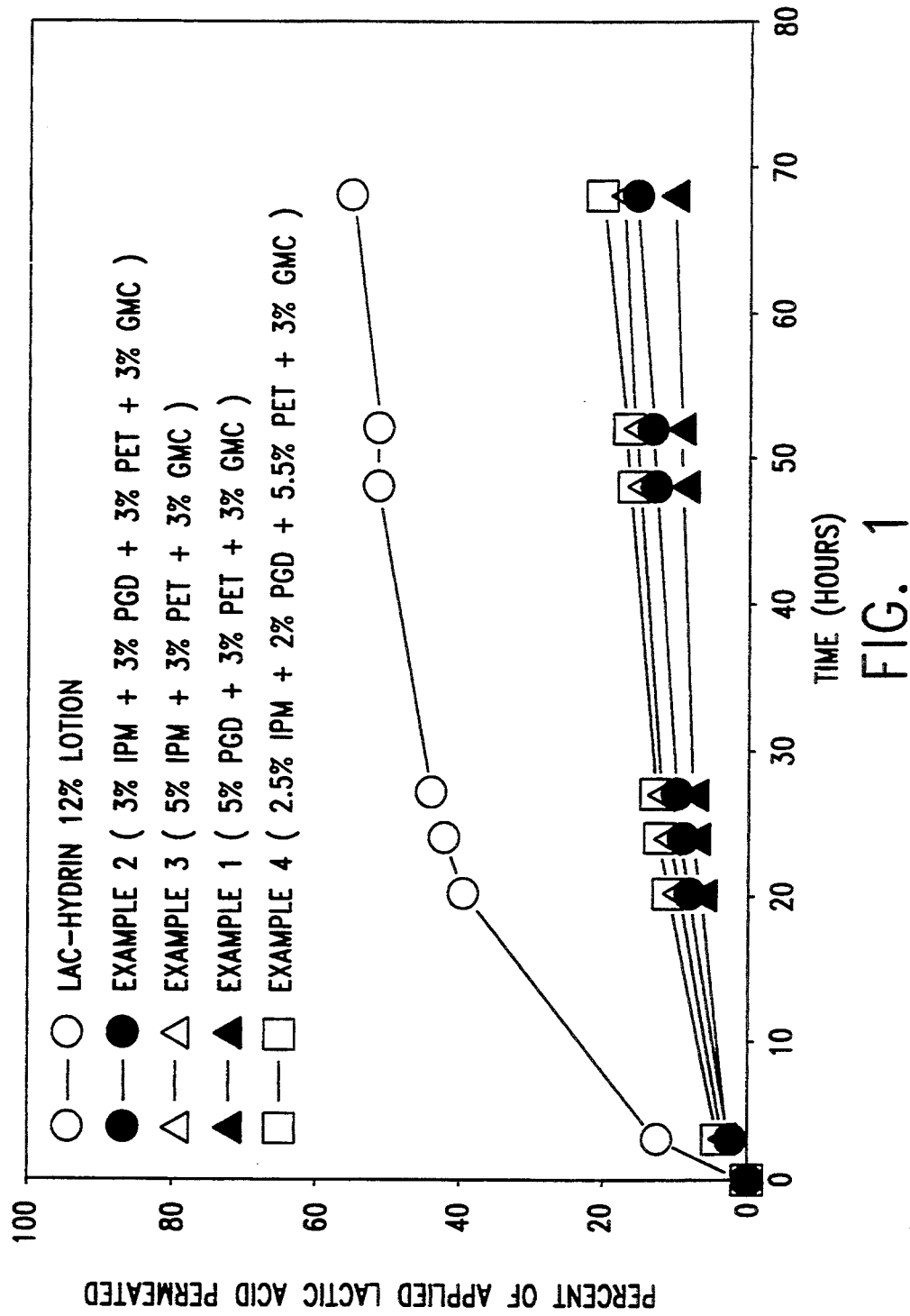
FIGS. 1 through 11 are graphs which will assist in understanding the improved properties of the compositions and methods of this invention.

The compositions employed in this invention are useful for all known utilities for topical administration of α-hydroxyacids. These include, for example treatment of dry skin, xerosis, ichthyosis, dandruff, acne, keratoses, psoriasis, wrinkles, warts, blemished skin, hyperpigmented skin, inflammatory dermatoses, eczema, pruritis, hyperkerotic skin, lentigines, melasma, age spots, laxity, leathery texture, roughness, sallow complexion, scaling, telangiectasia, mottled pigmentation, skin atrophy caused by steroids, and skin changes associated with intrinsic aging and photodamage.

The term "dermatological disorders", as used herein, refers to any of those cited above as well as other conditions treated by cosmetologists or dermatologists with α-hydroxy acids or salts thereof, in particular amphoteric amino acid salts of such acids. It includes skin conditions the treatment of which might usually be regarded as cosmetic, such as the treatment of hyperpigmented skin areas, as well as more serious skin conditions, such as chronic or acute psoriasis.

In addition to the α-hydroxy acid amphoteric salt, the compositions of the invention may contain any of a large number of additional cosmetic and pharmaceutical agents, provided that such additional agents are inert with respect to the formation, stability and activity of the α-hydroxy acid salts of the invention, i.e., they are reaction inert.

Cosmetic and pharmaceutical agents include those that improve or eradicate age spots, keratoses and wrinkles; analgesics; anesthetics; antiacne agents; antibacterials; antiyeast agents; antifungal agents; antiviral agents, antidandruff agents; antidermatitis agents; antipruritic agents; antiinflammatory agents; antihyperkeratolytic agents; antidryskin agents; antiperspirants; antipsoriatic agents; antiseborrheic agents; hair conditioners and hair treatment agents; antiaging and antiwrinkle agents; antiphotoaging agents; antiasthmatic agents and bronchodilators; sunscreen agents; antihistamine agents; skin lightening agents; depigmenting agents; vitamins; corticosteroids; tanning agents; hormones; retinoids; and topical cardiovascular agents.

Examples of cosmetic and pharmaceutical agents are clotrimazole, ketoconazole, miconazole, griseofulvin, hydroxyzine, diphenhydramine, pramozine, lidocaine, procaine, monobenzone, erythromycin, tetracycline, clindamycin, meclocycline, hydroquinone, 4-hydroxyanisole, minocycline, naproxen, ibuprofen, theophylline, cromolyn, albuterol, all trans retinoic acid, 13-cis retinoic acid, hydrocortisone, hydrocortisone 21-acetate, hydrocortisone 17-valerate, hydrocortisone 17-butyrate, betamethasone valerate, betamethasone dipropionate, triamcinolone acetonide, fluocinonide, clobetasol propionate, halobetasol propionate, benzoyl peroxide, crotamiton, propranolol, promethazine, vitamin A palmitate, vitamin E acetate and calcipotriene.

The salts of this invention may be employed with any of a variety of dermatologically acceptable carriers or excipients normally employed in compositions for topical administration, These are well known to the skilled artisan and include, for example, surfactants, emulsifiers, stabilizers, preservatives, antiseptics, emollients, thickeners, lubricants, humectants, chelating agents, fragrances and skin permeation enhancers.

The compositions may be in the form of solutions, emulsions, suspensions, lotions, creams, gels, sticks, ointments, liposomes, aerosol sprays, polymeric gels, plasters, patches, films or tapes, the preparation of which are well known to those skilled in the art of topical pharmaceutical formulation.

Examples of suitable emulsifiers include, steareth-2, steareth-21, polyoxyethylene-4-lauryl ether, polyethylene glycol-23-lauryl ether, sorbitan monostearate and polyoxyethylene-20-sorbitan monostearate. Examples of preservatives include, methyl paraben, propyl paraben, sorbic acid, potassium sorbate, benzyl alcohol, diazolidinyl urea, methylisothiazolinone and methylchloroiosothiazolinone.

Examples of emollients include, silicone oils, mineral oil, cocoa butter, hexyl laurate, diisopropyl adipate, dibutyl adipate, glyceryl stearate, beeswax, lanolin, sperm wax, cetyl palmitate, isopropyl myristate, isopropyl palmitate, isopropyl isostearate and propylene glycol dioctanoate.

Among the thickening agents there may be mentioned by way of example, xanthan gum brine tolerant, xanthan gum, and gum acacia, which are excellent as emulsion stabilizers and gelling agents.

Acceptable humectants include, for example, propylene glycol, glycerin, butylene glycol and polyethylene glycols.

As will be recognized by the skilled artisan, the term "effective amount" relates to the condition under treatment. Some conditions may require treatment with large amounts of α-hydroxy acid salts. Others may be effectively treated with smaller amounts. The treatment may require one or multiple dosage units applied all at once or over a period of time. Generally, the dosage requirements will be of the order of magnitude normally employed with similar treatments using α-hydroxy acid salts. However, because of the rapid onset of permeation and higher permeation concentration achieved, it is often possible to use lesser amounts of α-hydroxy acid salts, in accordance with the procedures of the present invention. In any event, the skilled artisan will have no difficulty in determining an "effective amount" for the treatment of a specific condition, by the application of the routine test procedures normally employed.

The advantages of this invention will be readily apparent from the following description taken together with the results illustrated in the figures.

The results to be described were based on skin permeation and skin retention tests, since a principal object of the invention is that the lactic acid permeate into the skin but that a sufficient amount of it be retained therein to be therapeutically effective.

The skin permeation test was conducted by the following procedure:

In-vitro Skin Permeation Study $^{14}$C-L-lactic acid sodium salt and $^{14}$C-DL-lactic acid sodium salt were used in the skin permeation study. The test formulations with L-lactic acid salts and DL-lactic acid salts were spiked and mixed with $^{14}$C-L-lactic acid sodium salt and $^{14}$C-DL-lactic acid sodium salt, respectively, to result in a radioactive concentration of 6 microcurie per ml.

Franz Diffusion Cell Study at Finite Dose

For each formulation, skin sections were mounted on three or four flat flange Franz diffusion cells (FDC 400) with a diffusional cross-section area of 1.2cm$^2$. About 60 to 100 mg of test formulation were placed on the stratum corneum surface of the skin in the donor compartment and the receptor compartment was filled with about 11 ml of normal saline. The receptor fluid was well stirred throughout the experiment and the temperature was maintained by circulating water at 37° C. through the water jacket of the diffusion cells. Precisely 500 $\mu$l of receptor fluid was collected in a scintillation vial at appropriate intervals for a period of 68 hours. Fifteen ml of scintillation fluid (INSTA-GEL XF PACKARD) were added directly to the scintillation vials and the lactic acid content was determined on a Beckman LS 3801 scintillation counter. The receptor fluid was replenished after each withdrawal. All the receptor fluid and replenished fluids were filtered using a 0.22 $\mu$m filter and thoroughly degassed before use.

Preparation of Epidermis and Dermis for Analysis

After the skin permeation study, the stratum corneum surface of the skin was washed three times with 0.5 ml of water. Cotton swabs were used during the rinsing procedure to recover the remaining surface dose. A circular incision was made in the skin exposed to the formulation. The epidermis at the circular edge was slowly lifted using a pointed flat spatula, and then separated from the dermis using forceps. The epidermis and dermis were transferred to previously weighed teflon tape and dried in a desiccator for 72 hours until a constant weight was obtained. Known weights of epidermis and dermis were transferred to scintillation vials, 2 ml of SOLUENE-350 were added, and the vials were shaken at 40° C. until the skin samples were completely dissolved. The samples were then decolorized by adding 0.2 ml of $H_2O_2$ (30% solution) and refrigerated for two hours, Fifteen ml of HIONIC FLUOR solution were then added to the vials and they were then stored in complete darkness at 5° C. for 12 hours before counting. Refrigeration in darkness was necessary to avoid any chemiluminescence.

As indicated above, a principal object of this invention is to achieve a skin permeation and skin retention profile of lactic acid from amphoteric amino acid lactates comparable to that of lactic acid from ammonium lactate. As noted earlier, contrary to the teaching in U.S. Pat. No. 5,091,171, ammonium lactate has excellent lactic acid skin permeation and skin retention profiles and is very effective for treating dermatological disorders such as those mentioned above. As noted earlier, it has also been found, contrary to the teaching of U.S. Pat. No. 5,091,171, that amphoteric salts of $\alpha$-hydroxy acid, such as amino acid salts of $\alpha$-hydroxy acid, do not have advantageous $\alpha$-hydroxy acid skin permeation profiles as compared with the ammonium salts of the corresponding $\alpha$-hydroxy acid. In point of fact, the amphoteric amino acid salts of $\alpha$-hydroxy acids have much poorer $\alpha$-hydroxy acid skin permeation profiles than the ammonium salts of such $\alpha$-hydroxy acids.

It has now been found, unexpectedly, that it is possible to obtain improved $\alpha$-hydroxy acid skin permeation and retention profiles with lysine lactate and other amphoteric amino acid salts of $\alpha$-hydroxy acids by incorporating such salts in compositions having a specific pH range and containing defined quantities of GMC.

The specific pH range of operability for the compositions of this invention is from about 3 to 9, preferably about 3.5 to 6.5, and most preferably about 3.8 to 5.

The specific concentration range of GMC for the compositions of this invention is from about 0.5 to 8%, preferably about 1 to 7%, and most preferably about 2 to 5%.

It has been observed that, when operating within these defined ranges, it is possible to effect a degree of lactic acid skin permeation and retention which is comparable to that obtained with ammonium lactate. Within the ranges and at constant pH, it is possible to increase lactic acid skin permeation and retention by increasing the GMC content of the compositions. It is similarly possible to increase lactic acid skin retention and skin permeation by decreasing the pH while maintaining a constant GMC content.

Some variation from the defined ranges is possible. However, appreciable variation from the defined pH values may cause skin irritation with some patients. If the GMC content is too low, the desired results are not achieved. If it is too high, the cost of the compositions may be too high in relation to the improved results. Generally, for optimum results, it is preferred to operate towards the higher end of the defined range of GMC.

As recognized in U.S. Pat. Nos. 5,041,437, 5,059,427 and 5,073,369, GMC is known to assist the skin permeation of several therapeutic agents. There is, however, no predictability as to whether permeation enhancers such as GMC will assist in the permeation of a particular therapeutic agent. As shown in U.S. Pat. No. 4,732,892, valine is another material that is known to enhance skin permeation. However, in the absence of GMC, valine does not enhance skin permeation of lactic acid from a composition containing lysine lactate. It is, in fact well recognized by those skilled in the art that skin permeation enhancers that are useful with one therapeutic agent are not predictably useful with another agent. Moreover, GMC has been used principally to achieve complete permeation of the therapeutic agent through the skin for systemic distribution thereof. There has been no prior recognition of the presently discovered relationship between GMC content and pH or that this relationship pertains to both skin permeation and skin retention of $\alpha$-hydroxy acids from their amphoteric salts, particularly the amino acid salts. For the treatment of dermatological disorders with $\alpha$-hydroxy acids, the desidiratum is not systemic distribution. Rather, it is that the $\alpha$-hydroxy acid permeate into the skin and be retained there.

Typical compositions of this invention will contain a salt of a DL-$\alpha$-hydroxy acid, such as DL-lactic acid, and a L-amino acid, such as L-lysine, because lactic acid is commercially available as the racemic mixture and lysine is commercially available as the L-enantiomer. However, either of the enantiomers of the selected acids can be used to form the salt. The salt can also be formed from a racemic mixture of the selected amino acid. Lysine in the L-form is the presently preferred amino acid for use in this invention, although other amino acids, both natural and synthetic, are also useful. Typically useful amino acids include, lysine, histidine, arginine, ornithine and 4-amino butyric acid.

The reactants used to form the useful salts of this invention may be pure enantiomers, either D or L, or they may be mixtures of enantiomers, including racemic mixtures.

This invention, for purposes of illustration, has been described principally as applicable to $\alpha$-hydroxy acid salts of amino acids, such as the preferred embodiment, lysine lactate. It is, however, applicable to salts of other dermatologically useful $\alpha$-hydroxy acids, such as lactic acid, glycolic acid, citric acid tartaric acid and malic acid. It is applicable not only to natural and synthetic amino acids, but also to other amphoteric organic compounds which will form salts with such $\alpha$-hydroxy acids, particularly nitrogen containing amphoteric organic compounds particularly amino group containing compounds which also contain an available reactive carbonyl group. These include dipeptides, polypeptides and proteins which contain at least one basic group, such as the amino group, or others including, for example imino, guanidino, imidazolino, imidazolyl or other basic groups which permit the formation of amphoteric salts with selected $\alpha$-hydroxy acids.

Typically useful $\alpha$-hydroxy acids include, alkyl $\alpha$-hydroxy acids, aralkyl and aryl $\alpha$-hydroxy acids, polyhydroxy $\alpha$-hydroxy acids and polycarboxylic $\alpha$-hydroxy acids. Acids which may be mentioned by way of example, include, methyllactic acid, 2-hydroxypentanoic acid, $\alpha$-hydroxylauric acid, $\alpha$-hydroxystearic acid, mandelic acid, benzilic acid, 3-hydroxy-4-methoxymandelic acid, glyceric acid and saccharic acid.

Preferred for most applications are lactic acid, glycolic acid, citric acid, tartaric acid and malic acid. More preferred acids are lactic acid and glycolic acid. They are readily available and give consistently good results, most preferred is lactic acid.

The useful salts of this invention may be formed, for example, from lecithin and related types including, for example, phosphatidyl ethanolamine, phosphatidyl serine and sphingomyaline and other bases, such as carnosine (alanylhistidine), 4-aminobutanoic acid and citrulline (α-amino-α-ureidovaleric acid).

Representative amino acids that can be used to form salts of α-hydroxy acids, such as lactic acid include for example, glycine, alanine, valine, leucine, isoleucine, serine, threonine, cysteine, cystine, ornithine and tryptophan. Preferred salts of the invention are α-hydroxy salts of the basic amino acids lysine, histidine and arginine with lactic acid or glycolic acid.

It should be noted that unless otherwise indicated, when reference is made to percent by weight, in the description of this invention and in the claims that follow, it means percent by weight based on the total weight of the composition.

Table 1 shows the compositions of four lysine lactate 12% test lotions containing a number of ingredients, the most important of which, for purposes of this description, are lysine lactate, petrolatum (PET), propylene glycol dioctanoate (PGD), isopropyl myristrate (IPM) and glyceryl monocaprylate (GMC). It will be noted that all of the compositions contain the same amount of GMC and all have a pH of 4.6, but they differ in the amount of petrolatum and the amount of emollients isopropyl myristate and propylene glycol dioctanoate.

General Description of Preparing Amino Acid Lactate Emulsified Lotion Formulations 1) In a first vessel, disperse xanthan gum BT in propylene glycol.
2) In a second vessel, disperse magnesium aluminum silicate (VEEGUM K) in water and then, while mixing, slowly add step 1 xanthan gum BT mixture while maintaining the temperature at 65°–70° C.
3) In a third vessel, heat the oil components, such as petrolatum, glyceryl monocaprylate, isopropyl myristate, PG-dioctanoate, dimethicone, steareth-2, steareth-21, cetyl alcohol and stearyl alcohol, to 65° to 70° C. and mix until uniform.
4) In a fourth vessel heat lysine lactate solution to 35°–40° C., and then, with rapid mixing, slowly disperse titanium dioxide in it.
5) With rapid mixing, add step 3) oil phase slowly to step 2) water phase. Mix for about 5 to 10 minutes and then cool to 50°–55° C. Then, while mixing, add sorbic acid and begin cooling to 48°–50° C.
6) To step 5) mixture at 48°–50° C., with rapid mixing, add slowly the step 4) lysine lactate mixture. Mix while permitting the temperature to fall below 35° C.

It should be noted that the aforementioned process is preferred as it assists in appropriate incorporation of lysine lactate and xantham gum BT. The xanthan gum BT is an excellent emulsion stabilizer.

TABLE 1

Composition of experimental lotions containing lysine lactate equivalent to 12% wt of lactic acid

| Ingredients % w/w | EXAMPLE 1 | EXAMPLE 2 | EXAMPLE 3 | EXAMPLE 4 |
|---|---|---|---|---|
| Lysine Lactate* | 50.00 | 50.00 | 50.00 | 50.00 |
| Titanium Dioxide | 0.15 | 0.15 | 0.15 | 0.15 |
| Petrolatum | 3.0 | 3.0 | 3.0 | 5.5 |
| PG Dioctanoate | 5.0 | 3.0 | — | 2.0 |
| Steareth-2 | 2.0 | 2.0 | 2.0 | 2.0 |
| Steareth-21 | 3.0 | 3.0 | 3.0 | 3.0 |
| Cetyl Alcohol | 0.5 | 0.5 | 0.5 | 0.5 |
| Stearyl Alcohol | 5.0 | 5.0 | 5.0 | 5.0 |
| Dimethicone 200 | 1.0 | 1.0 | 1.0 | 1.0 |
| Isopropyl Myristate | — | 3.0 | 5.0 | 2.5 |
| Glyceryl Monocaprylate | 3.0 | 3.0 | 3.0 | 3.0 |
| Propylene Glycol | 5.0 | 5.0 | 5.0 | 5.0 |
| Xanthan Gum BT | 0.4 | 0.4 | 0.4 | 0.4 |
| VEEGUM K | 0.3 | 0.3 | 0.3 | 0.3 |
| Water | 21.45 | 20.45 | 21.45 | 20.45 |
| Sorbic Acid | 0.2 | 0.2 | 0.2 | 0.2 |
| pH | 4.6 | 4.56 | 4.6 | 4.60 |

*A solution containing 27.27 grams of lactic acid (88% active), 32.3 grams of lysine monohydrate, water QS 100 grams, the monomer content of the lactic acid being at least 91%.

FIG. 1 shows the permeation profile of the four compositions of Table 1 compared to that of ammonium lactate commercially available from Westwood-Squibb as LAC-HYDRIN 12% lotion. It will be noted that during the entire period of the test the permeation of lactic acid from ammonium lactate was appreciably higher from ammonium lactate than from lysine lactate contained in any of the four test compositions.

Figure 2:
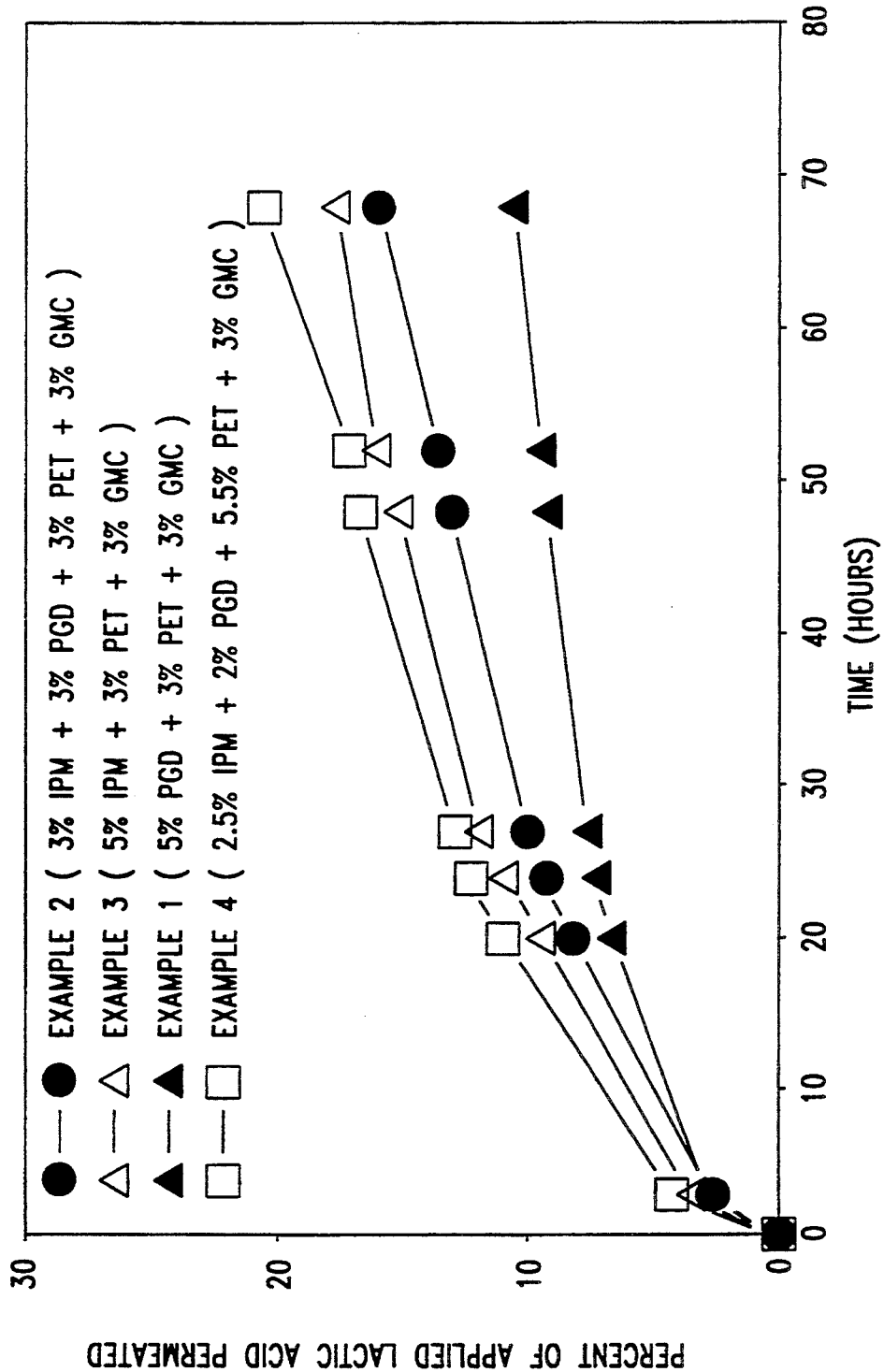

FIG. 2 is a scaled up version of FIG. 1 showing on the abscissa the lactic acid skin permeation range from 0 to 30% instead of the 0 to 100% range of FIG. 1. The enlarged scale shows that there are, in fact, differences in skin permeation of lactic acid from compositions all of which are at a pH of 4.6 and contain 3% percent by weight GMC. These differences may be attributed to variations in the amounts of other components in the compositions, such as PET, IPM and PGD.

Figure 3:
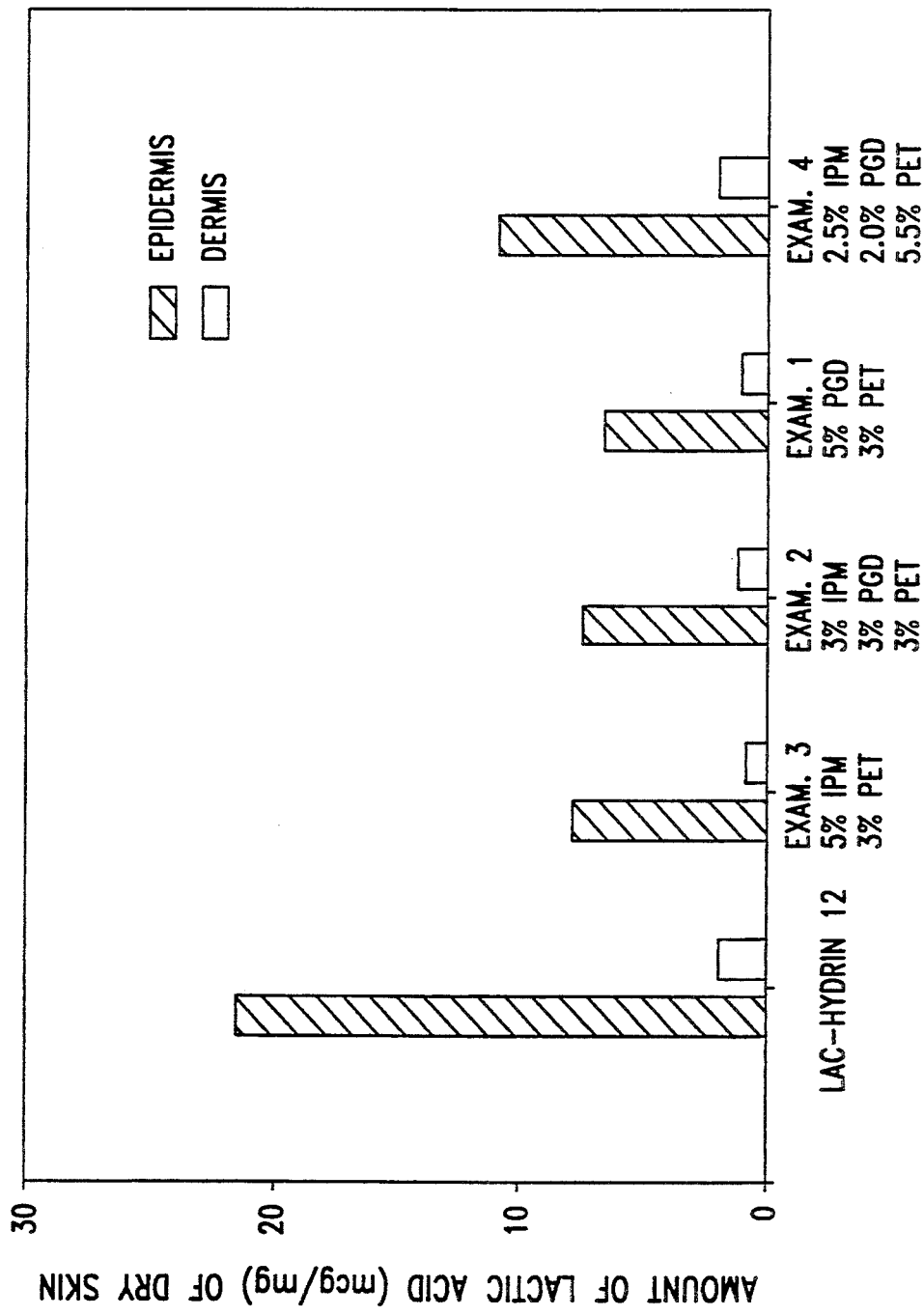

FIG. 3 shows the results of lactic acid skin retention studies on the same compositions shown in FIG. 1. From the graphs it will be seen that there is excellent skin retention of lactic acid from the compositions containing ammonium lactate. It will be seen, also, that at constant GMC content and pH, there is variation in skin retention which, again, may be attributed to variation in the amounts of PET, IPM and PGD in the compositions. Under the conditions of the test, it is clear that increased PET content markedly increases both skin permeation and skin retention of lactic acid from lysine lactate.

Of the formulations tested, the composition of Example 4 was the best in both skin permeation and skin retention of lactic acid. It is also apparent that IPM is a better skin permeation enhancer for lactic acid than PGD.

The data of Table 2, which follows, demonstrates that the lactic acid permeation from the composition of Example 4 can be improved by decreasing pH or by increasing GMC concentration.

TABLE 2

Compositions of experimental lysine lactate lotions containing lysine lactate equivalent to 12% lactic acid

| Ingredients % w/w | EXAMPLE 5 | EXAMPLE 6 |
|---|---|---|
| Lysine Lactate Solution A* | 40.0 | — |
| Lysine Lactate Solution B** | — | 40.0 |
| Titanium Dioxide | 0.15 | 0.15 |
| Petrolatum | 5.5 | 5.5 |
| Isopropyl Myristate | 2.5 | 2.5 |
| PG-Dioctanoate | 2.0 | 2.0 |
| Steareth-2 | 2.0 | 2.0 |
| Steareth-21 | 3.0 | 3.0 |
| Stearyl Alcohol | 4.0 | 4.0 |
| Dimethicone 200 | 1.0 | 1.0 |
| Glyceryl Monocaprylate | 3.0 | 4.0 |

TABLE 2-continued

Compositions of experimental lysine lactate lotions
containing lysine lactate equivalent to 12% lactic acid

| Ingredients % w/w | EXAMPLE 5 | EXAMPLE 6 |
|---|---|---|
| Cetyl Alcohol | 0.5 | 0.5 |
| Propylene Glycol | 5.0 | 4.0 |
| Xanthan Gum BT | 0.4 | 0.4 |
| VEEGUM K | 0.3 | 0.3 |
| Water | 30.45 | 30.45 |
| Sorbic Acid | 0.2 | 0.2 |
| pH | 4.0 | 4.6 |

*A solution containing:
lactic acid (88%) 34.0 gm
lysine monohydrate 27.0 gm
water qs 100 gm
The monomer content of the lactic acid being at least 91%
**A solution containing:
lactic acid (88%) 34.0 gm
lysine monohydrate 40.37 gm
water qs to 100 gm
The monomer content of the lactic acid being at least 91%

It is evident from a comparison of Tables 1 and 2 that the composition of Example 5 is substantially the same as that of Example 4, except for the decreased pH (which is achieved by changing the lactic acid to lysine ratio), and that the composition of Example 6 is substantially the same as that of Example 4, except for the increase in GMC content from 3% to 4%.

Figure 4:
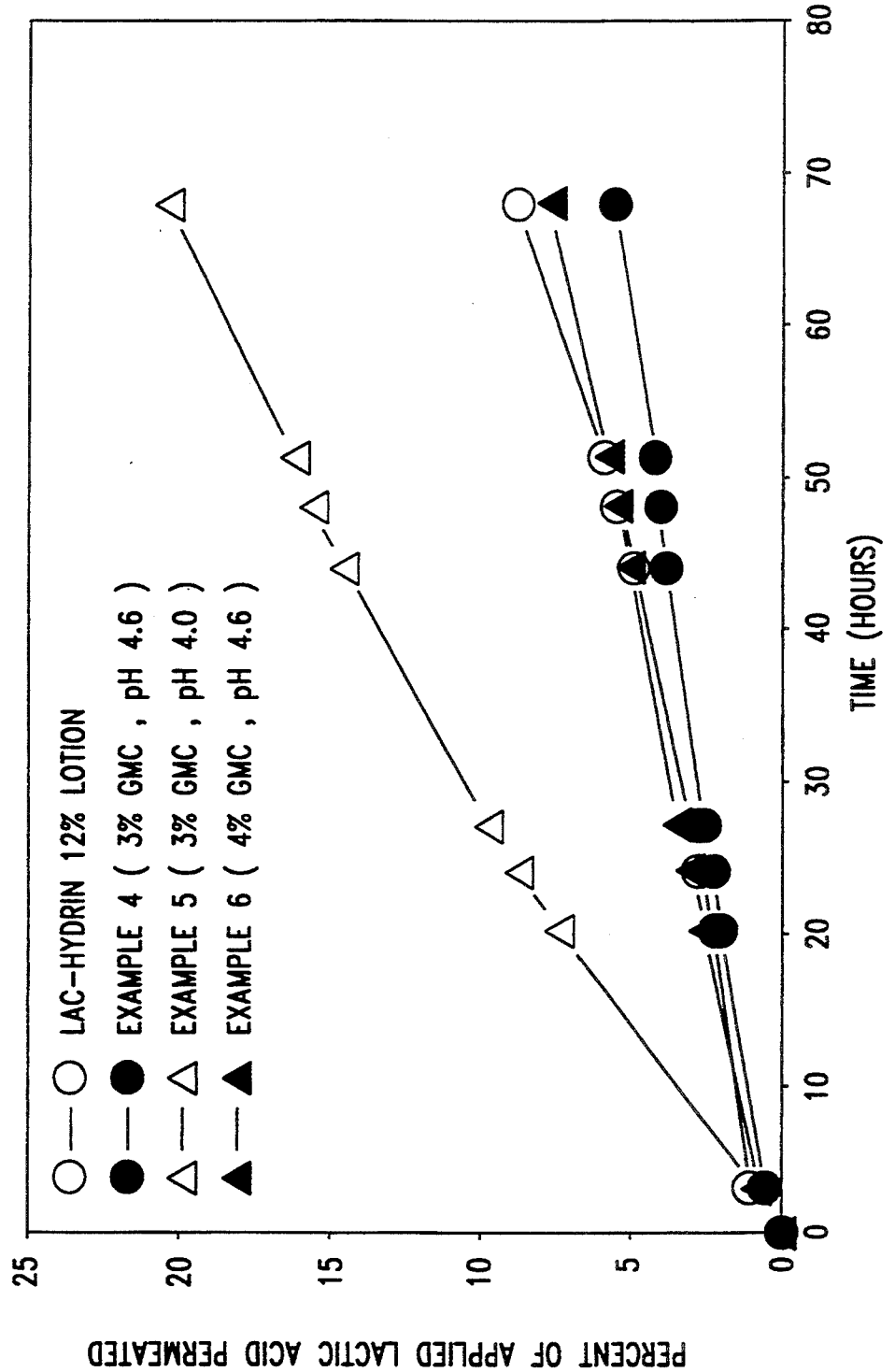

FIG. 4 shows that a decrease in pH, while maintaining the GMC content at a constant value, remarkably increases the skin permeation of lactic acid to a value higher than that for ammonium lactate lotion and that increasing the GMC content at the same pH produces compositions which have substantially the same permeation profile as ammonium lactate (LAC-HYDRIN 12% lotion).

Figure 5:
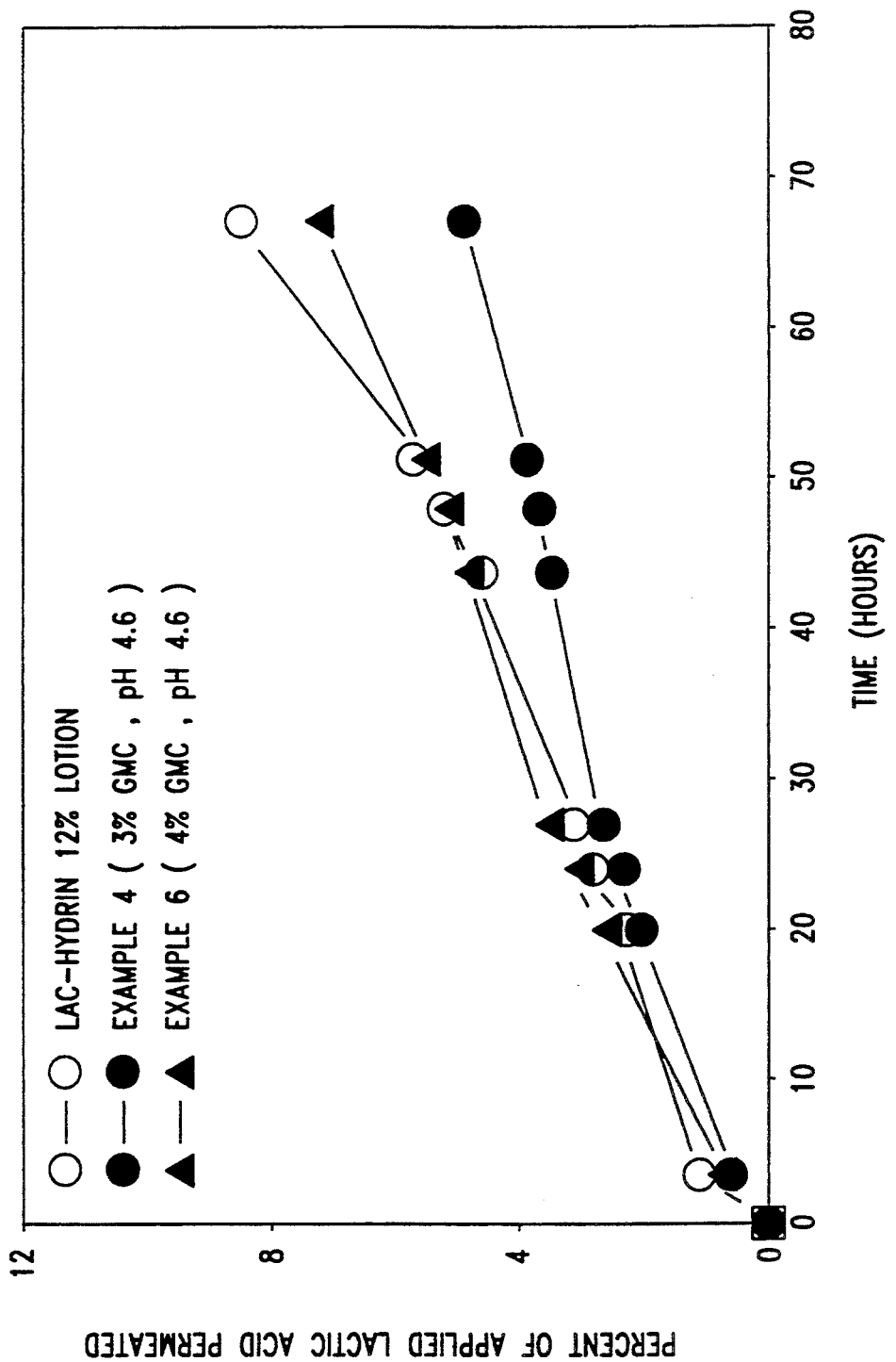

FIG. 5 is similar to FIG. 4 but on an enlarged scale with respect to the abscissa. It further confirms the conclusions reached concerning increased GMC content at constant pH and concerning decreasing the pH of the composition at constant GMC content.

Figure 6:
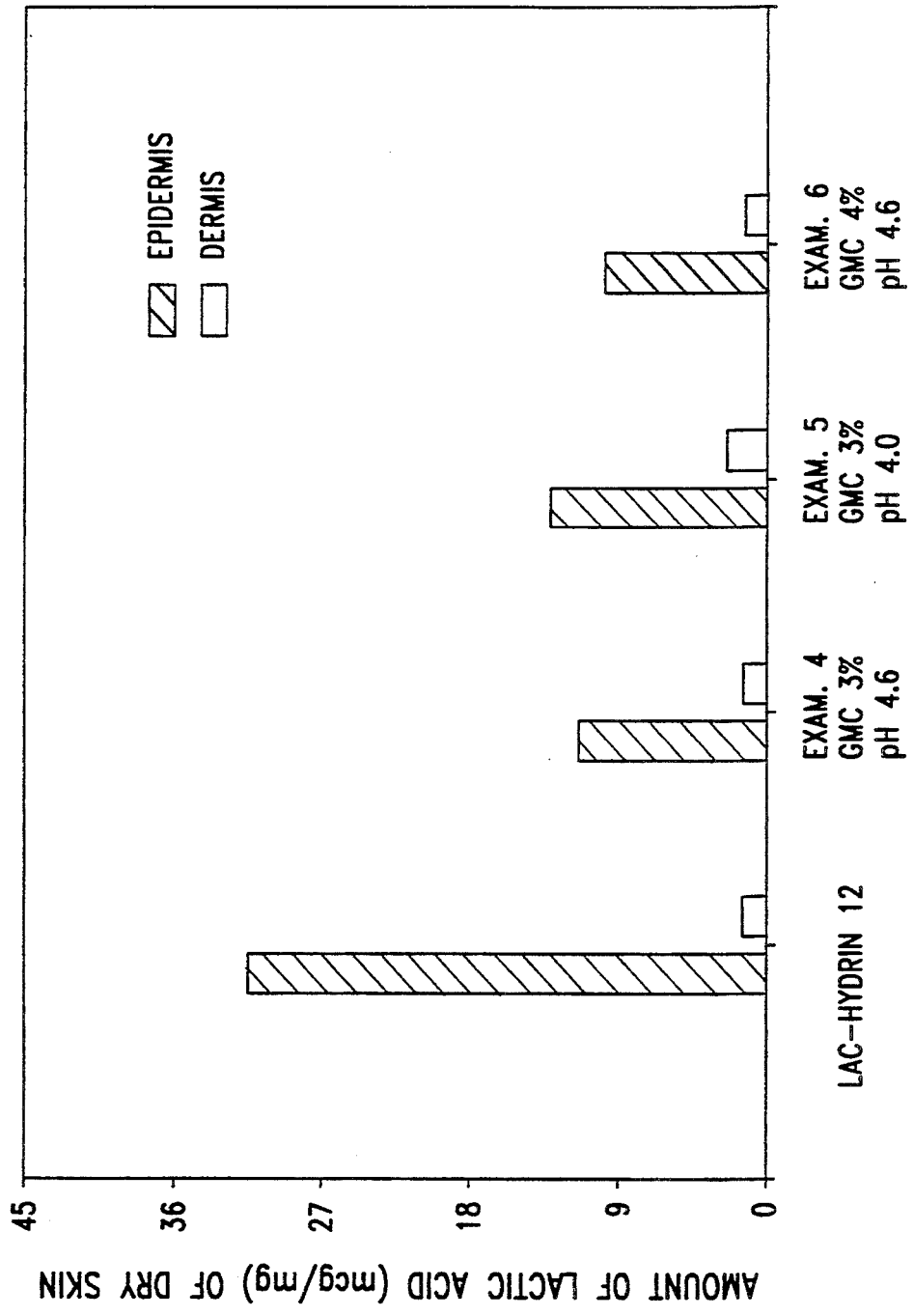

FIG. 6 shows the results of a skin retention test on the same compositions studied to produce the skin permeation results shown in FIGS. 4 and 5. Although LAC-HYDRIN is best for skin retention, it is evident that a reduction in pH and an increase in GMC content improves skin retention of lactic acid.

FIGS. 7 through 11 record the results of similar studies which further support the unexpected finding of the relationship between GMC content and pH, the discovery of which permits control of both skin retention and skin permeation of lactic acid.

The first group of compositions studied are shown in Table 3.

TABLE 3

Composition of solution formulations containing
L-lysine and L-histidine salts of
12% DL- and L-lactic acid.

| Ingredients % w/w | EXAMPLE 7 | EXAMPLE 8 | EXAMPLE 9 | EXAMPLE 10 |
|---|---|---|---|---|
| DL-Lactic Acid (88%) | 13.6 | 13.6 | — | — |
| L-Lactic Acid (88%) | — | — | 13.6 | 13.6 |
| L-Histidine | 16.52 | — | 16.52 | — |
| L-Lysine H2O | — | 16.14 | — | 16.14 |
| Water QS | 100.00 | 100.00 | 100.00 | 100.00 |
| pH | 4.76 | 4.63 | 4.81 | 4.69 |

Method: Mix lactic acid, amino acid and water until uniform. Heat to 60–65° C. and mix for 25 minutes, then mix while cooling to room temperature, QS with water and measure the pH.

Figure 7:
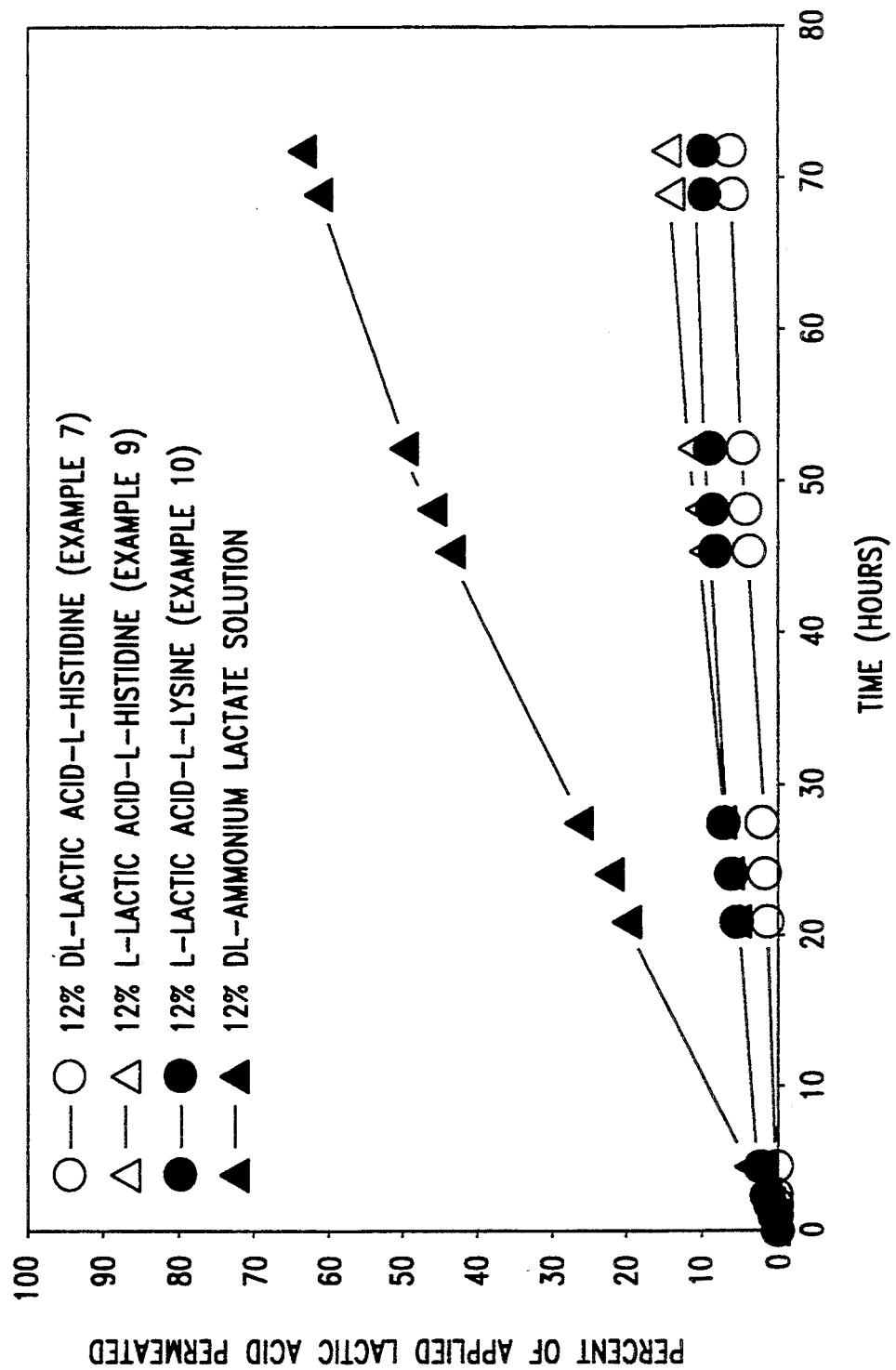

FIG. 7 shows the lactic acid skin permeation profiles of the compositions of Table 3 and of 12% DL-ammonium lactate solution. From the figure and the table, it will be apparent that permeation of lactic acid from ammonium lactate is significantly higher than from the amino acid salts of lactic acid.

Figure 8:
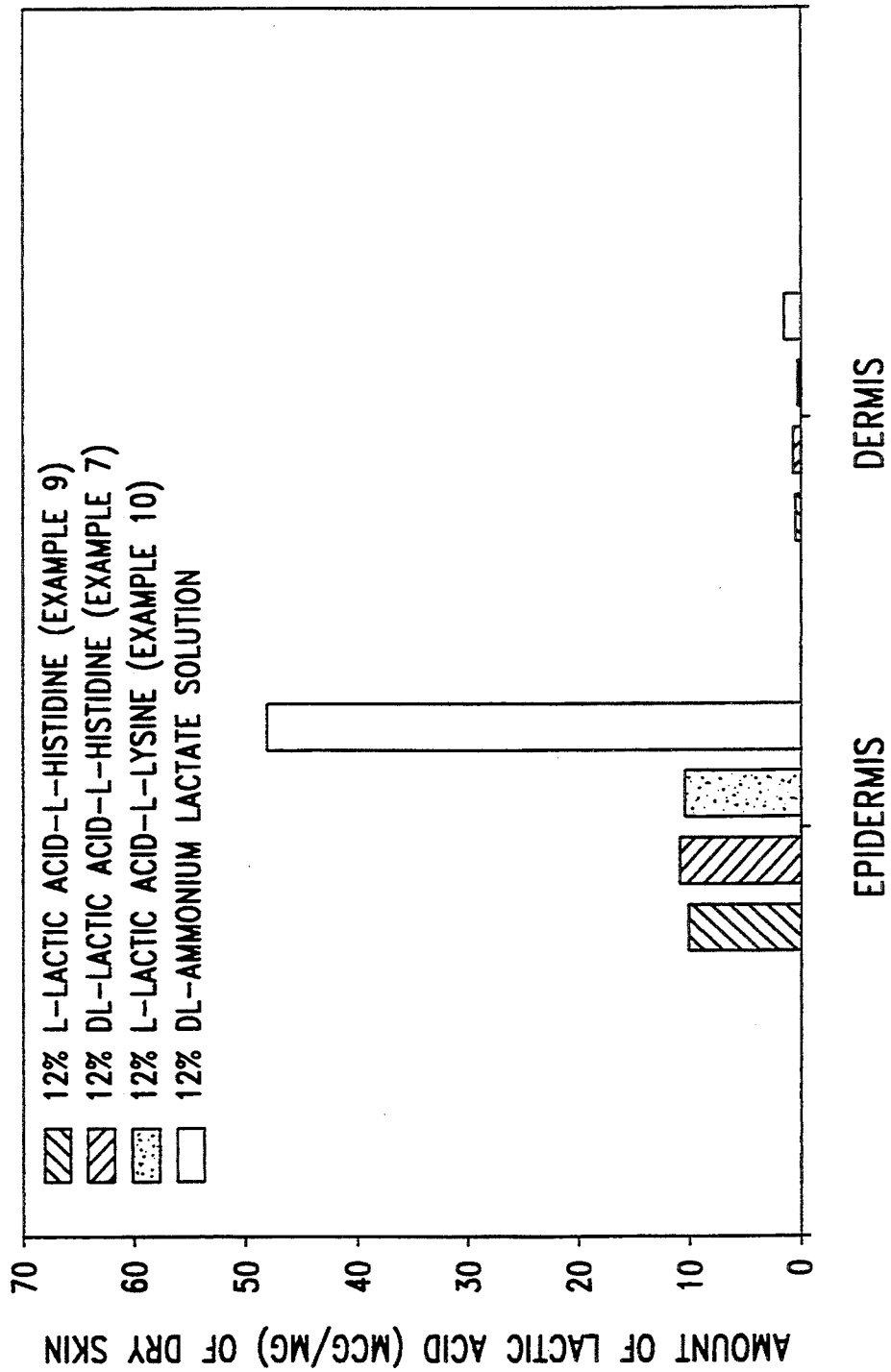

FIG. 8 shows a similar result with respect to lactic acid skin retention of the four compositions of Examples 7 through 10.

In summary, FIGS. 7 and 8 show that skin permeation of lactic acid from amphoteric amino acid lactate is 7 to 10 fold less than from ammonium lactate and that lactic acid epidermal retention is five fold less with amphoteric amino acid lactate as compared to ammonium lactate.

Table 4 shows the formulations of the next compositions studied. The study was designed to evaluate the influence of GMC and pH on skin retention of lactic acid from amino acid lactates. It will be noted that the pH increases from the composition of Example 11 to those of Examples 13 and 14, but that the pH of the compositions of Examples 13 and 14 remains constant. The compositions of Examples 11, 12 and 13 are free of GMC, whereas the composition of Example 14 contains 2.5% by weight of GMC. The increase in pH is accomplished by increasing the concentration of lysine in the composition. All these solution compositions were heated at 60° C. for 5 days to hydrolyze lactalate esters of lactic acid so that the final composition has a lactic acid monomer content greater than 91% of total lactic acid.

TABLE 4

Compositions of solutions containing lysine
lactate equivalent to 12% DL-lactic acid

| Ingredients % w/w | EXAMPLE 11 | EXAMPLE 12 | EXAMPLE 13 | EXAMPLE 14 |
|---|---|---|---|---|
| DL-Lactic Acid (88%) | 13.6 | 13.6 | 13.6 | 13.6 |
| L-Lysine H2O | 4.3 | 16.14 | 20.0 | 20.0 |
| Glyceryl monocaprylate | — | — | — | 2.5 |
| Water qs | 100.00 | 100.00 | 100.00 | 100.00 |
| pH | 3.0 | 4.2 | 5.0 | 5.0 |

Method: Mix DL-lactic acid, L-Lysine-H2O in water until uniform. Then heat in closed container for 5 days at 60° C. Cool to room temperature, then add glyceryl monocaprylate and mix well.

Figure 9:
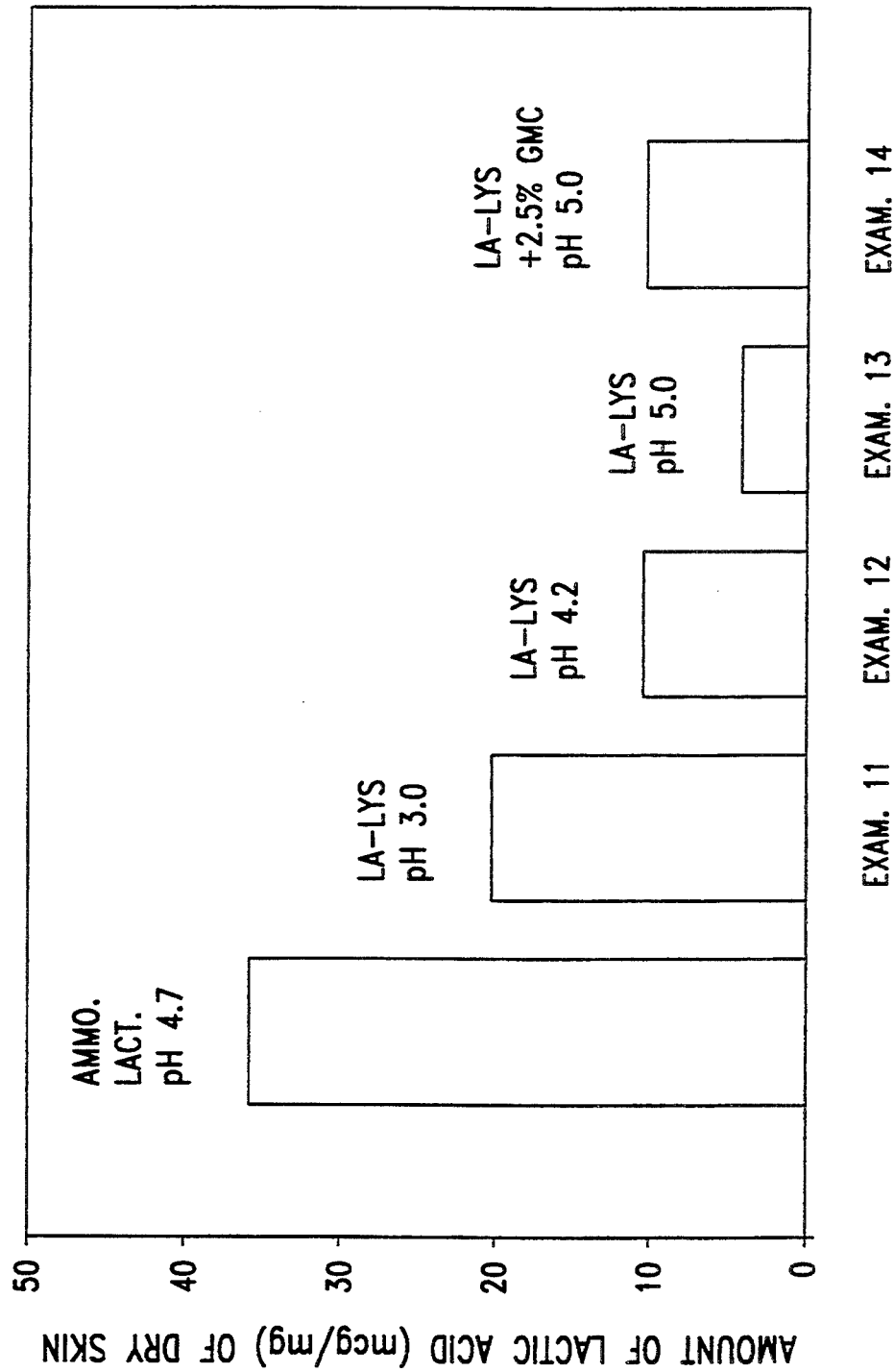

FIG. 9 shows the skin retention of lactic acid for the compositions of Examples 11 through 14 of Table 4 and for 12% ammonium lactate solution. It will be seen that ammonium lactate at pH 4.7 is the best composition for lactic acid skin retention. It is also apparent that skin retention of lactic acid from lysine lactate solution is increased by 5-fold when the pH of the composition is decreased from pH 5 (Example 13) to pH 3 (Example 11). At constant pH 5, the retention of lactic acid from lysine lactate was increased about 2.5 fold by the addition of GMC (Example 14).

The compositions of Table 5 were prepared to study the effect of decreasing pH at a fixed GMC content.

TABLE 5

Solution compositions containing lysine
lactate equivalent to 12% tactic acid

| Ingredients % w/w | EXAMPLE 15 | EXAMPLE 16 | EXAMPLE 17 |
|---|---|---|---|
| DL-Lactic Acid (88%) | 13.6 | 13.6 | 13.6 |
| L-Lysine H2O | 4.8 | 16.14 | 20.0 |
| Glyceryl Monocaprylate | 2.5 | 2.5 | 2.5 |
| Water QS | 100.00 | 100.00 | 100.00 |

TABLE 5-continued

| | Solution compositions containing lysine lactate equivalent to 12% lactic acid | | |
|---|---|---|---|
| Ingredients % w/w | EXAMPLE 15 | EXAMPLE 16 | EXAMPLE 17 |
| pH | 3.2 | 4.2 | 5.0 |

Method: Mix DL-lactic acid and L-lysine H₂O with water until uniform. Then heat in a closed container at 60° C. for 5 days. Cool to room temperature, then add glyceryl monostearate and mix well.

Figure 10:
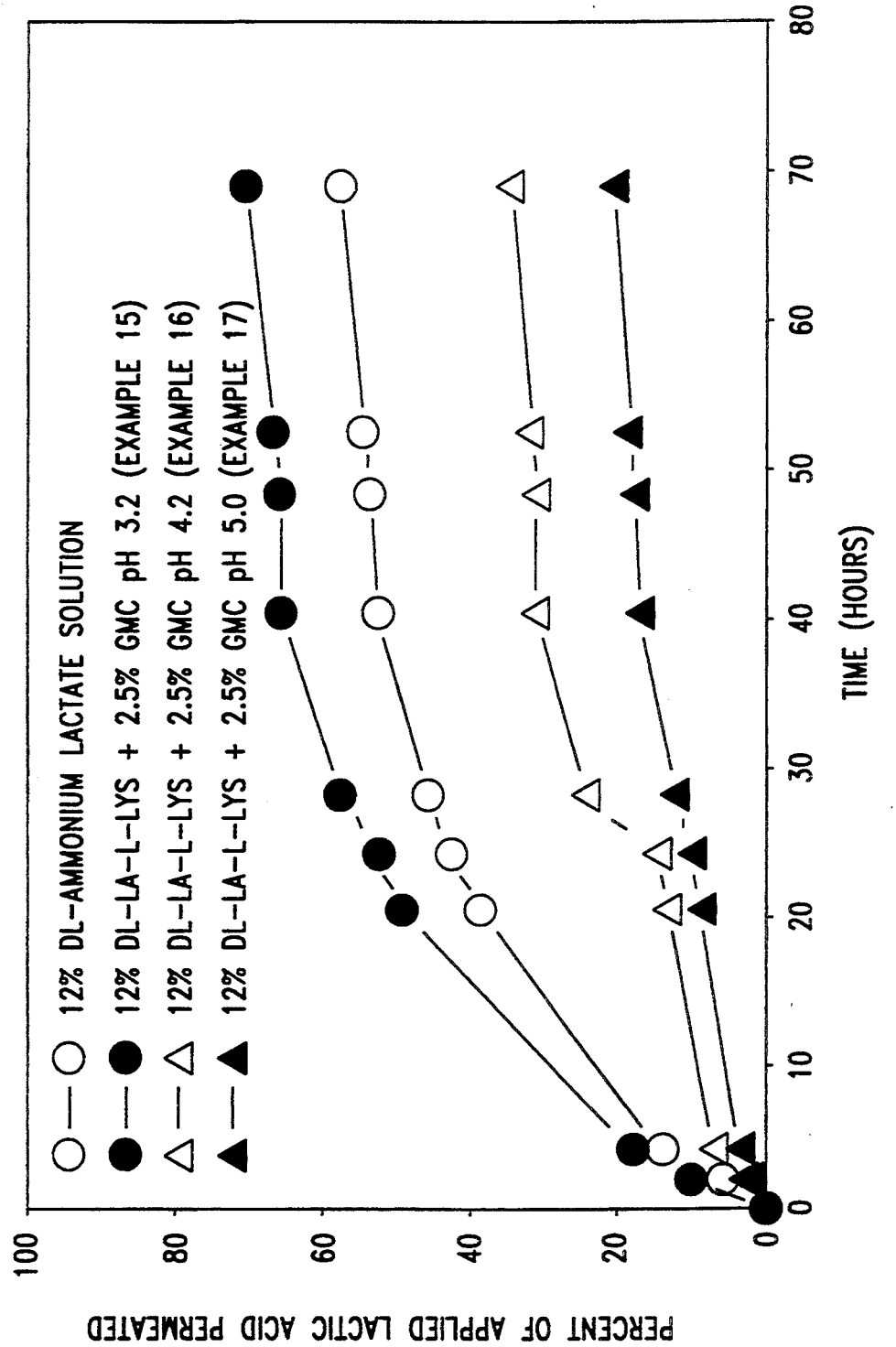

FIG. 10 shows the skin permeation profile of the compositions of Table 5 and for 12% ammonium lactate solution. It will be seen that at a fixed GMC content of 2.5% by weight, the skin permeation profile was increased by 3.5 fold when the pH was decreased from 5 (Example 17) to 3.2 (Example 15). Most important of all, the lactic acid skin permeation profile of the composition of Example 15 at pH 3.2 was during the entire period of the study, better during the entire period of the study than the lactic acid skin permeation profile of ammonium lactate.

Figure 11:
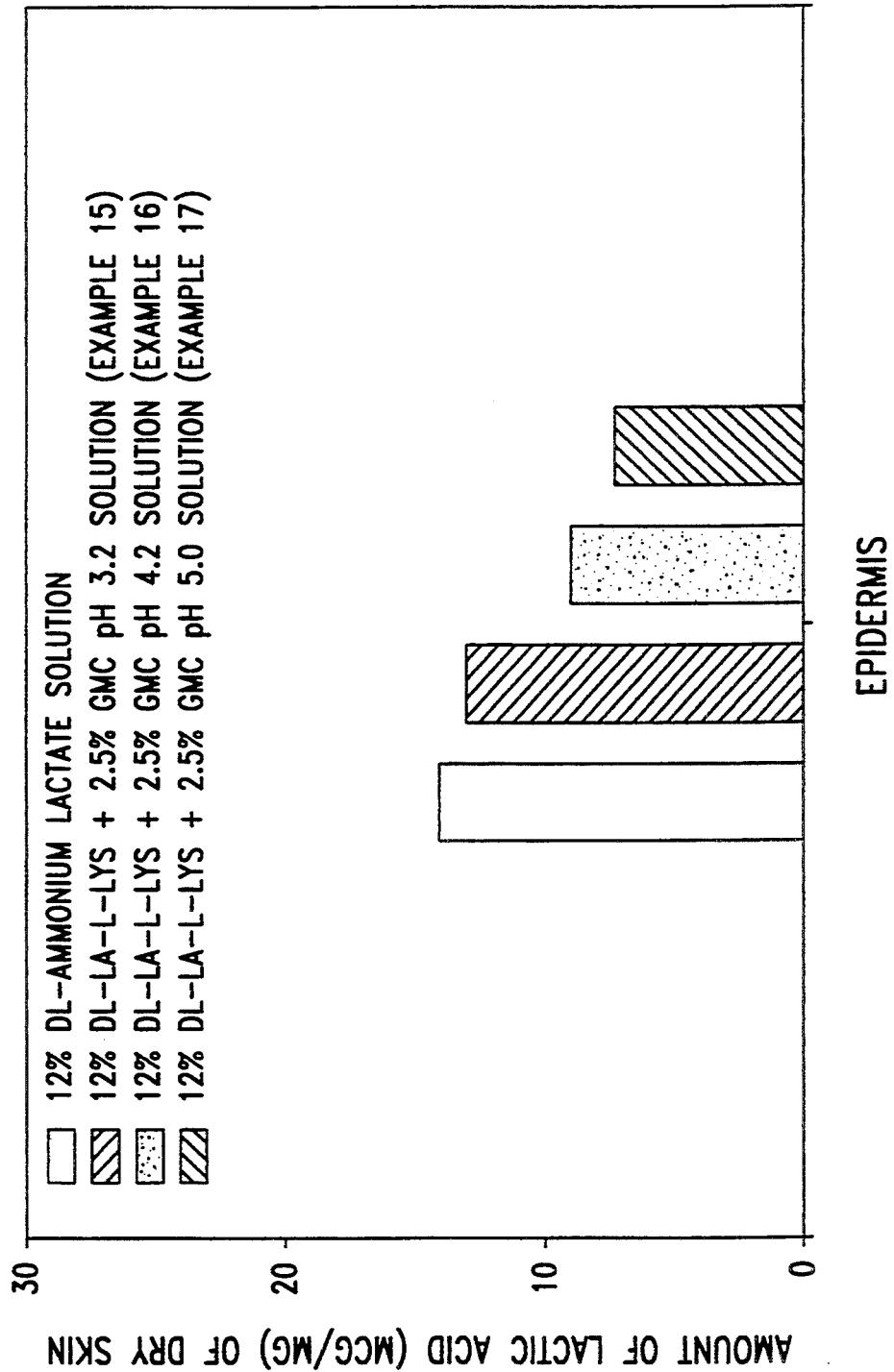

FIG. 11 shows exactly the same profile for skin retention; i.e., skin retention of lactic acid from lysine lactate solutions was increased by 2.5 fold when the pH was decreased from 5 to 3.2 at a constant GMC content of 2.5%. The skin retention of lactic acid from the lysine lactate pH 3.2 composition was equivalent to that from the ammonium lactate composition.

From the results of the studies described herein, it is apparent that it is possible to optimize skin permeation and skin retention of lactic acid from compositions containing amino acid salts of lactic acids by manipulation of pH and GMC content within defined ranges. It is further evident that it is possible to achieve skin permeation and retention values for lactic acid that are at least comparable to and with some compositions even better than can be achieved with the use of ammonium lactate. Similar results are achieved with other compositions of the invention.

It is also clear that increasing the IPM content and/or the PET content of the compositions further improves lactic acid skin permeation and lactic acid skin retention. Petrolatum is an occlusive agent and is known to hydrate the skin and enhance permeation of highly oil soluble compounds. With water soluble compounds like methanol and ethanol, permeation is unaltered by hydration. With a compound such as propranolol hydration decreases the permeation rate by two fold. Thus petrolatum's enhancement of the permeation of lactic acid and other α-hydroxy acids from their highly water soluble amphoteric salts, expecially their amino acid salts, is surprising.

The amounts of PET and IPM which will be effective to further enhance the skin permeation and skin retention of α-hydroxy acids from specific compositions of this invention may be readily determined by a few simple observations by one skilled in the formulation art. With PET, the amount is typically from about 0 to 80%, preferably 1 to 20%, most preferably 3 to 10%. For IPM, the amount is typically from about 0 to 30%, preferably 0.5 to 15%, most preferably 2 to 10%. Mixtures of PET and IPM can be employed.

What is claimed is:

1. A topical composition for the treatment of a dermatological disorder comprising a dermatologically effective amount of an amphoteric salt of an α-hydroxy acid selected from the group consisting of lactic acid, glycolic acid, citric acid, tartaric acid and malic acid and a compound selected from the group consisting of amino acids, dipeptides, polypeptides and proteins, in a dermatologically acceptable carrier which contains from about 0.5 to 8% glyceryl monocaprylate, from about 0 to 80% petrolatum and from about 0 to 30% isopropyl myristrate, the pH of the composition being from about 3 to 9.

2. The composition as claimed in claim 1 wherein the α-hydroxy acid is lactic acid or glycolic acid.

3. The composition as claimed in claim 1 wherein the amino acid is lysine, histidine or arginine.

4. The composition as claimed in claim 1, 2 or 3 wherein the α-hydroxy acid is lactic acid, the compound is lysine, the composition contains from 1 to 7% glyceryl monocaprylate, from 1 to 20% petrolatum, and from 0.5 to 15% isopropyl myristate and the pH of the composition is from 3.5 to 6.5.

5. A method for enhancing skin permeation and skin retention of an α-hydroxy acid selected from the group consisting of lactic acid, glycolic acid, citric acid, tartaric acid and malic acid which comprises applying to the skin a composition containing an amphoteric salt of such acid with a compound selected from the group consisting of amino acids, dipeptides, polypeptides and proteins, in a dermatologically acceptable carrier which contains from about 0.5 to 8% glycerol monocaprylate, from about 0 to 80% petrolatum and from about 0 to 30% isopropyl myristrate the pH of the composition being from about 3 to 9.

6. The method as claimed in claim 5 wherein the α-hydroxy acid is lactic acid or glycolic acid.

7. The method as claimed in claim 5 wherein the amino acid is lysine, histidine or arginine.

8. The method as claimed in claim 5 wherein the α-hydroxy acid is lactic acid, the compound is lysine, composition contains from 1 to 7% glyceryl monocaprylate, from 1 to 20% petrolatum, and from 0.5 to 15% isopropyl myristrate and the pH of the composition is from 3.5 to 6.5.

9. A method of treating a dermatological condition comprising applying to skin of a mammal effected by such condition a composition comprising an amount effective to treat such condition of a salt of an α-hydroxy acid selected from the group consisting of lactic acid, glycolic acid, citric acid, tartaric acid and a compound selected from the group consisting of amino acids, dipeptides, polypeptides and proteins, in a dermatologically acceptable carrier which contains from about 0.5 to 8% glyceryl monocaprylate, from about 0 to 80% petrolatum and from about 0 to 30% isopropyl myristrate, the pH of the composition being from about 3 to 9.

* * * * *